US00PP23977P2

(12) United States Plant Patent
Rinck

(10) Patent No.: US PP23,977 P2
(45) Date of Patent: Oct. 8, 2013

(54) ***CANNA* PLANT NAMED 'B MARLEY'**

(50) Latin Name: *Canna americanallis*
Varietal Denomination: B Marley

(76) Inventor: Michael C. Rinck, Tavares, FL (US)

( * ) Notice: Subject to any disclaimer, the term of this patent is extended or adjusted under 35 U.S.C. 154(b) by 93 days.

(21) Appl. No.: 13/374,966

(22) Filed: Jan. 25, 2012

(51) Int. Cl.
*A01H 5/00* (2006.01)

(52) U.S. Cl.
USPC ..... Plt./415

(58) Field of Classification Search
USPC ..... Plt./415
See application file for complete search history.

*Primary Examiner* — Susan McCormick Ewoldt
(74) *Attorney, Agent, or Firm* — Penny J. Aguirre

(57) ABSTRACT

A new cultivar of *Canna* plant named 'B Marley', that is characterized by its foliage that is highly variegated with stripes of dark green, red, yellow, orange and bright green with a green mid rib with leaves maturing to dark green with mauve striping, its flowering stems that are a blend of maroon in color and green in color, its highly suckering growth habit, its compact plant habit in width, and its flowers that are orange with a thin reddish orange margin on its staminodes.

2 Drawing Sheets

Botanical classification: *Canna americanallis.*
Cultivar designation: 'B Marley'.

BACKGROUND OF THE INVENTION

The present invention relates to a new and distinct cultivar of *Canna americanallis* known as 'B Marley', and is hereinafter referred to as 'B Marley'.

The Inventor discovered the new cultivar, 'B Marley', at a tissue culture production facility in May of 2011 in Eustis, Fla. 'B Marley' originated as a naturally occurring chimeral mutation of *Canna americanallis* 'Pretoria' (not patented).

Asexual reproduction of the new cultivar was first accomplished utilizing in vitro propagation by the Inventor in Eustis, Fla. in July of 2011. Asexual reproduction of the new cultivar has shown that the unique features of 'B Marley' are stable and reproduced true to type in successive generations.

SUMMARY OF THE INVENTION

The following traits have been repeatedly observed in trials in Eustis, Fla. and represent the characteristics of the new cultivar. These attributes in combination distinguish 'B Marley' as a new and unique cultivar of *Canna.*

1. 'B Marley' exhibits foliage that is highly variegated with stripes of dark green, red, yellow, orange and bright green. The leaves mature to dark green with mauve striping. The leaf mid rib is green in color.
2. 'B Marley' exhibits a highly suckering growth habit.
3. 'B Marley' exhibits a compact plant habit in width.
4. 'B Marley' exhibits flowers that are orange with a thin reddish orange margin on its staminodes.
5. 'B Marley' exhibits flowering stems that are a blend of maroon and green in color.

The parent plant, 'Pretoria', differs from 'B Marley' in having foliage that is variegated with green and white stripes, in being less suckering, in having orange flowers with a thin yellow margin on its staminodes, and in having flowering stems that are grey-green in color with an orange hue. 'B Marley' can be most closely compared to the cultivars 'Pink Sunburst' and 'Tropicanna' (both unpatented). Both are similar to 'B Marley' in rooting and grow rate, in having a similar leaf variegation pattern, and in having a similar flower shape. 'Pink Sunburst' differs from 'B Marley' in having leaves that are variegated with yellow, pink, and green stripes, in being shorter in height, and in having flowers that are pink in color. 'Tropicanna' differs from 'B Marley' in having leaves that are variegated with pink, red, green, yellow, orange, and burgundy with a mid rib that is yellow to orange in color, in being taller in height, in having bright orange flowers with a yellow margin on the staminodes, and in having flowering stems that are purple to reddish pink in color.

BRIEF DESCRIPTION OF THE DRAWING

The accompanying colored photographs illustrate the overall appearance and distinct characteristics of the new *Canna*. The photographs were taken of a 2 year-old plant as grown in a greenhouse in a 5-gallon container in Eustis, Fla.

Figure 1:
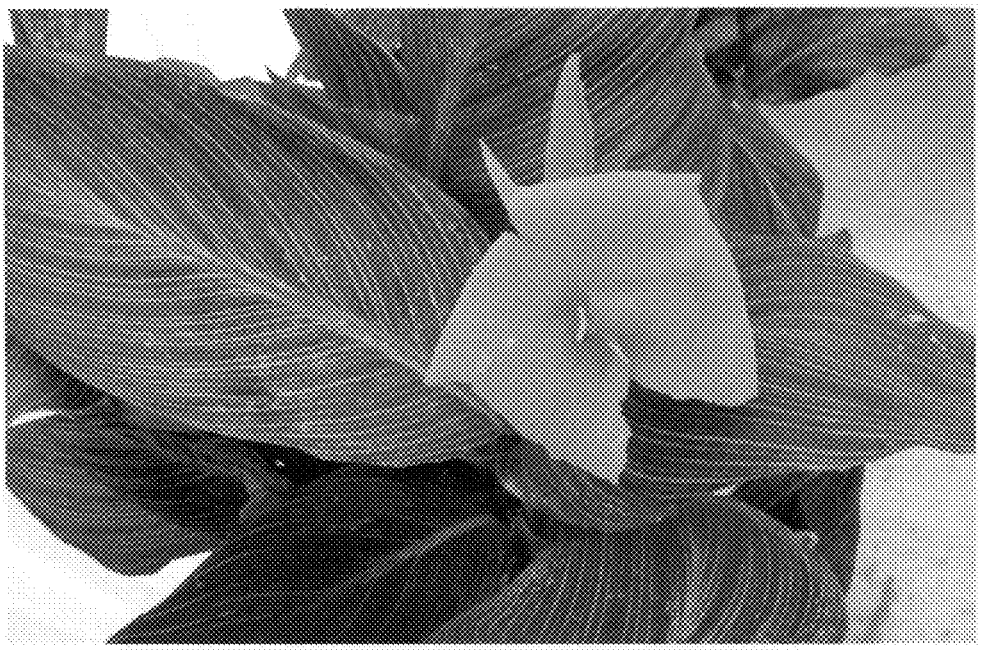
FIG. 1 provides a top view of a plant of 'B Marley' in bloom.
Figure 2:
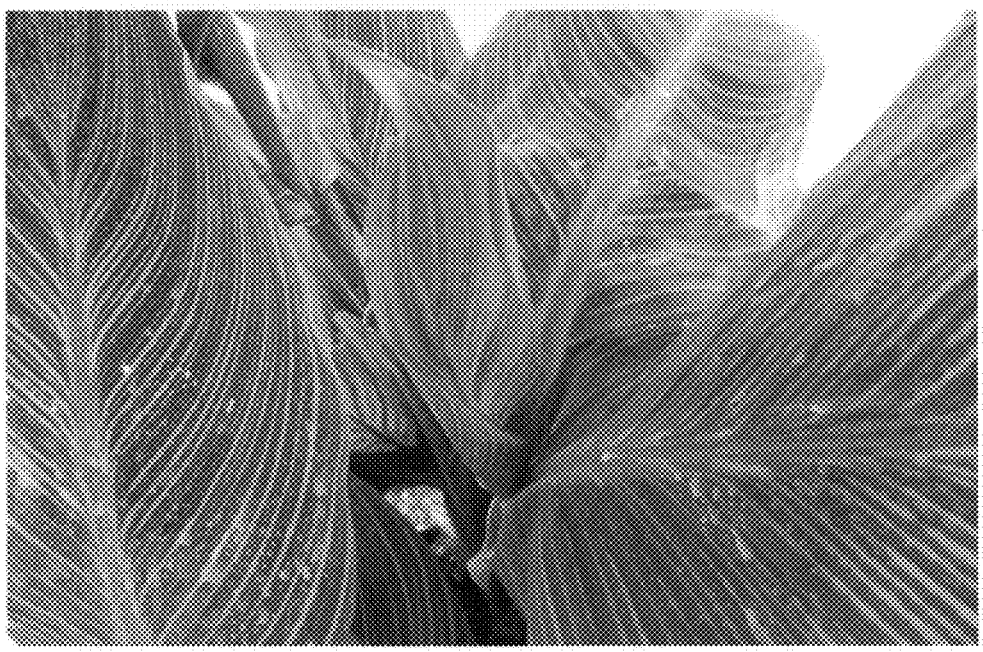

The photograph in FIG. 2 provides a view of young and maturing foliage of 'B Marley'.

Figure 3:
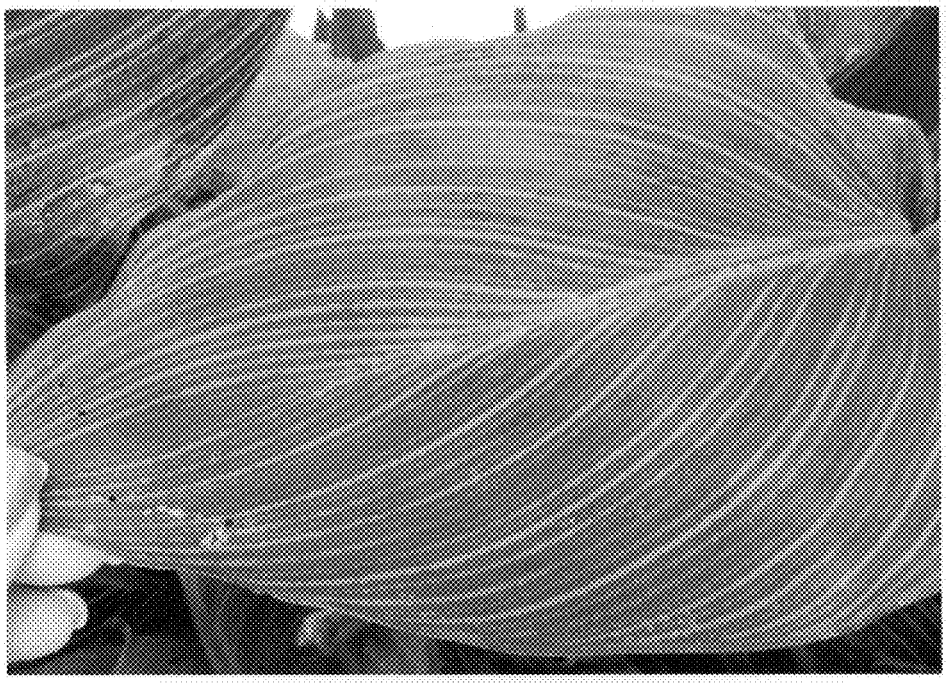

The photograph in FIG. 3 provides a close-up view of a mature leaf.

Figure 4:
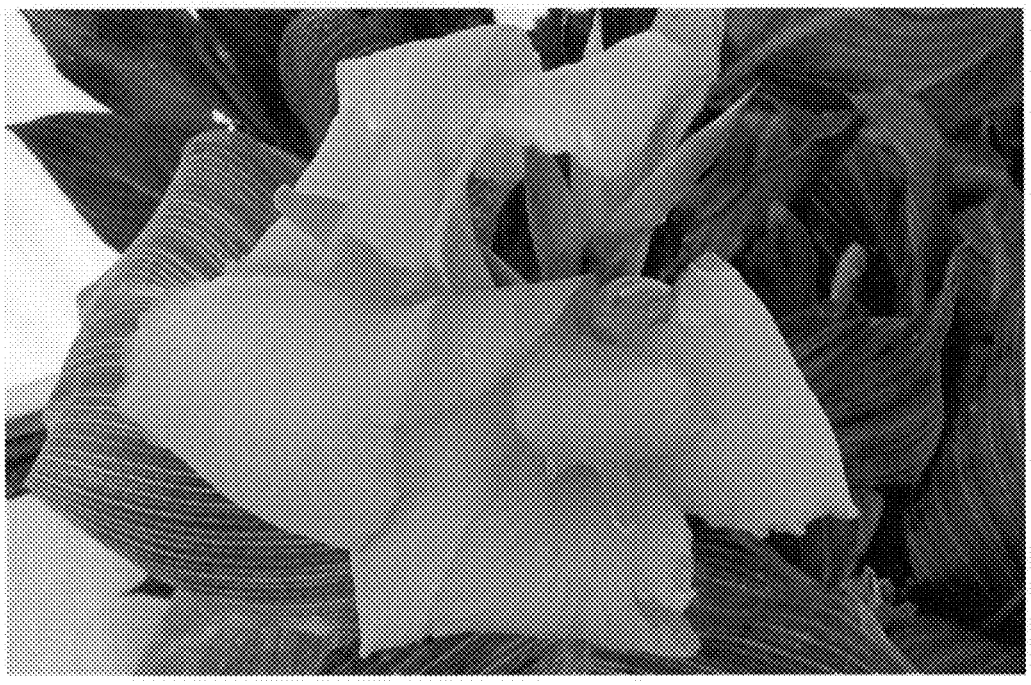

The photograph in FIG. 4 provides a view of an inflorescence of 'B Marley'. The colors in the photographs are as close as possible with the photographic and printing technology utilized and the color values cited in the Detailed Botanical Description accurately describe the colors of the new *Canna.*

DETAILED BOTANICAL DESCRIPTION OF THE PLANT

The following is a detailed description of two year-old plants of the new cultivar as grown outdoors in a greenhouse in Eustis, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—April to first frost in Florida.

*Plant type*.—Deciduous, tropical, perennial.

*Plant habit*.—Upright, tufted leaves on stout stems.

*Height and spread*.—Reaches 0.9 to 1.2 m in height and about 61 cm in width.

*Hardiness*.—U.S.D.A. Zones 7 to 11.

*Diseases and pests*.—Thick leaves impart an increased resistance to diseases and pests.

*Roots*.—Fleshly.

Propagation and growth:

*Propagation type*.—In vitro propagation is preferred.

*Growth rate*.—Fast growing (0.9 m in 6 to 8 weeks), numerous suckers produced, average of 35 per 5-gallon container.

*Root development*.—Roots develop in 10 days in a stage3 rooting media, fully develop in a 1-inch liner in 42 days, 1-inch liner fully develops in a 6-inch pot in 6 to 8 weeks.

Stem description:

*Stem size*.—An average of 28 cm in length and an average of 2.8 cm in width (with sheaths).

*Stem type*.—Stout, surrounded by sheathed leaf petioles.

*Stem color*.—Inner stem 145C and slightly flushed with 69C, stems are defined by color of outer petiole surface; a blending of N137A and 137A and 183A.

*Stem surface*.—Defined by outer petiole surface.

*New shoots*.—An average of 7 cm in length and 8 mm in width prior to first leaf unfurling, 183C in color.

Foliage description:

*Leaf shape*.—Elliptic to slightly ovate.

*Leaf division*.—Simple.

*Leaf base*.—Cuneate.

*Leaf apex*.—Acuminate with small mucronate tip.

*Leaf venation*.—Pinnate, mature leaves; mid rib on upper surface is conspicuous and 137C in color, mid rib on lower surface is conspicuous, protruding, and a blend of 174B and 174C and 144C in color, color of other veins match leaf coloration.

*Leaf margins*.—Entire, Slightly wavy.

*Leaf attachment*.—Petiolate.

*Leaf arrangement*.—Alternate with petioles sheathed.

*Leaf surface*.—Glabrous on upper surface and lower surface with a slight sheen on both surfaces on newer leaves.

*Leaf orientation*.—Emerge upright and become nearly horizontal and slightly cascading downward when mature.

*Variegation pattern*.—Intensely variegated with thin stripes pinnately radiating in numerous colors on upper and lower leaf surface, brightly colored stripes (an average of 1 mm in width) are separated by dark green stripes (of various widths ranging from 1 to 5 mm) with the larger dark green stripes with mauve stripes on mature leaves.

*Leaf color*.—New foliage, upper and lower surface; dark green stripes 136A and 139A, other stripes; 1A, 144C, 34B, 169B, 31B, and 31C, maturing foliage, upper surface; dark green stripes N189A and a color between N189A and 202A, other stripes; 144D, 169B, 31C, and 31D, maturing foliage, lower surface; dark green stripes N137A and a color between N189A and 202A, other stripes; 144D, 169B, 31C, 145D and 47D, fully mature foliage, upper and lower surface; stripes of N137A and 48D.

*Leaf size*.—Average of 33 cm in length and 20 cm in width when mature.

*Leaf quantity*.—An average of 10 per shoot 30 cm in length.

*Petioles*.—About 17 cm in length, an average of 2.5 mm in width, glabrous on inner and outer surface, sulcate and clasping to stem the entire length, color outer surface; a blending of N137A and 137A and 183A, color inner surface; thin vertical stripes of 145C and 145D.

Inflorescence description:

*Inflorescence type*.—Terminal raceme that elongates as individual flowers open; flowers with showy staminodes that are arranged spirally along the rachis and open sequentially during the bloom season.

*Inflorescence size*.—Average of 17 cm in length and 12 cm in diameter (dependant on number of blooms open).

*Flower buds*.—Linear to slightly narrow oblanceolate in shape, an average of 11 cm in length and 1 cm in width, color a blend of 183C, 182D, with minute vertical lines of 137C.

*Flower fragrance*.—None detected.

*Lastingness of inflorescence*.—Inflorescence blooms continuously during the bloom period, individual flowers last about 2 days.

*Flower quantity*.—Continuously produced throughout the bloom season, one to three open at one time, an average of 50 flowers produced in a season.

*Flower type*.—Comprised of less showy sepals and petals and showy staminodes.

*Flower size*.—Average of 10 cm in length and depth.

*Rachis*.—Average of 15 cm in length (includes peduncle about 4 mm in length) and 2 mm in diameter and an average of 6 mm in width, color a blend of 147A and 147B and suffused with 183B, glabrous surface, shape is oval and becoming flattened on one side near apex, an average of 2 bracts; an average of 10 cm in length and 3 cm in width, curled inward, glabrous on both surfaces, clasping base, apex acuminate with small mucronate tip, outer color is comprised on vertical stripes of 183D and 147A, inner color is comprised of thin vertical stripes of 145C, 137C and 183D.

*Sepals*.—3, lanceolate in shape, truncate base, acuminate apex, about 1.8 cm in length and 7 mm in width, 183D in color blending to 147A in centers, glabrous surface, persist after staminodes drop.

*Petals*.—3, lanceolate in shape, truncate base, acute apex, about 4 cm in length and 8 mm in width, both surfaces 161C in color and suffused with 183D (strongly at apex), glabrous surface, held upright with upper portion reflexed.

*Pedicels*.—Stout, 3 cm in length and 4 cm in width, glabrous surface, 144A in color.

*Staminodes*.—Sterile; 4, size; an average of 9.9 cm in length and 4.6 cm in width, obovate-elliptic in shape, apex round, base cuneate to narrower base about 2 cm in length and 1 cm in width with truncate base, margins slightly crenate (irregular) and wavy, color upper and lower surface; a blend of 24A and 42B and blends into 13B on basal region, glabrous on upper and lower surface, fertile male, 1, an average of 7.5 cm in length and 3 cm in width, renal in shape, apex round, base cuneate to narrower base about 1.5 cm in length and 5 mm in width with truncate base, margins slightly crenate (irregular) and wavy, color upper and lower surface; 24A and suffused with 42B that blends into 13B on basal region with a thin margin of 42B, glabrous on upper and lower surface, fertile female; staminode pistil as described under gynoecium.

Reproductive organs:

*Gynoecium*.—1 pistil, style is an average of 7.5 cm in length and 1 cm in width, narrowly club shaped, truncate base, margins smooth, color upper and lower surface; a blend of 24A and 42B and blends into 13B on basal region, glossy on upper and lower surface, stigma surrounds apex, is about 5 mm in length and 164D in color, ovary is inferior, about 9 mm in length and 4 mm in width, and 146C in color.

*Androcoecium*.—1 stamen, about 4.5 cm in length, filament is adnate to edge of staminode, a blend of 24A and 42B in color, about 3 cm in length, anthers are about 1.5 cm in length, slightly curved, 199D in color and basifixed, pollen is moderate in quantity and 164D in color.

*Fruit and seed*.—Capsule, globose, 147A in color, spiky surface, about 1.5 cm in length and width, seed formation was not observed.

It is claimed:

1. A new and distinct cultivar of *Canna* plant named 'B Marley' as herein illustrated and described.

* * * * *